United States Patent [19]
Kelly et al.

[11] Patent Number: 6,054,583
[45] Date of Patent: Apr. 25, 2000

[54] PREPARATION OF 2-SUBSTITUTED PYRIDINES

[75] Inventors: Martha Jean Kelly, Norristown; Damian Gerard Weaver, Lansdale, both of Pa.

[73] Assignee: Rohm and Haas Company, Phila., Pa.

[21] Appl. No.: 09/305,410

[22] Filed: May 5, 1999

Related U.S. Application Data

[60] Provisional application No. 60/084,685, May 8, 1998.

[51] Int. Cl.[7] .................. C07F 7/22; C07F 7/10; C07D 213/71; C07D 213/70
[52] U.S. Cl. ................. 546/14; 546/4; 546/294; 546/296; 546/298; 546/301; 546/302; 546/303; 546/314; 546/348
[58] Field of Search .................. 546/4, 14, 294, 546/296, 298, 301, 302, 303, 314, 348

[56] References Cited

FOREIGN PATENT DOCUMENTS 0 683 156 A1  5/1995  European Pat. Off. .

OTHER PUBLICATIONS

Dongwei, C., et al., "A Study of the Lithiation of 2,6–Dibromopyridine with Butyllithium, and its Application to Synthesis of L–739,010", *Tetrahedron Letters,* vol. 37, No. 15, pp. 2537–2540 (Apr. 8, 1996).

Gilman, H., et al., "Some 2–Pyridlmetallic Compounds", *Journal of Organic Chemistry,* vol. 16, pp. 1788–1791 (1951).

*Primary Examiner*—Patricia L. Morris
*Attorney, Agent, or Firm*—Clark R. Carpenter

[57] ABSTRACT

This invention relates to a process for preparing 2-substituted pyridines via metal halogen exchange with sec-butyllithium on optionally substituted 2-bromo or 2-iodopyridines. The resulting lithopyridine intermediate is reacted with an electrophile to provide the desired 2-substituted pyridine. The substitution of sec-butyllithium for n-butyllithium in such a process results in an enhanced yield and purity of the desired 2-substituted pyridine.

9 Claims, No Drawings

PREPARATION OF 2-SUBSTITUTED PYRIDINES

This application claims priority to Provisional Patent Application 60/084,685 filed May 8, 1998, now abandoned.

This invention relates to a process for preparing 2-substituted pyridines via metal halogen exchange with sec-butyllithium on optionally substituted 2-bromo or 2-iodopyridines. The resulting lithopyridine intermediate is reacted with an electrophile to provide the desired 2-substituted pyridine.

The reaction of a 2-bromo or a 2-iodopyridine with n-butyllithium is well known in the art. However, such a procedure can result in only a poor yield of the desired 2-substituted pyridine product which additionally suffers from low purity. We have unexpectedly discovered that the substitution of sec-butyllithium for n-butyllithium in such a process results in an enhanced yield and purity of the desired 2-substituted pyridine.

EP 0 683 156 A1 discloses the preparation of 2-acetyl-5-chloropyridine from 2-bromo-5-chloropyridine using n-butyllithium as the lithiation agent followed by reaction with N,N-dimethylacetamide to provide the product. However, this reference does not teach or suggest the use of sec-butyllithium as the lithiation reagent with its attendant advantages.

This invention provides a process for preparing a 2-substituted pyridine of formula (I)

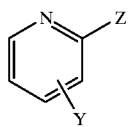

(I)

comprising the steps of
(i) reacting a 2-substituted pyridine of formula (II)

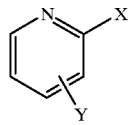

(II)

, with sec-butyllithium to form a 2-lithopyridine intermediate of formula (III)

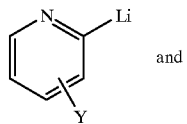

(III)

and (ii) reacting a 2-lithopyridine intermediate of formula (III) with an electrophile to form a 2-substituted pyridine of formula (I) wherein
X is bromo or iodo,
each Y is a group that is not reactive with the lithium compound under the reaction conditions used and
Z is the residue of the electrophile.

In a preferred embodiment, each Y is independently selected from the group consisting of a hydrogen atom, fluoro, chloro, alkyl, fluoroalkyl, trichloromethyl, alkoxy, fluoroalkoxy, alkylthio, fluoroalkylthio, N,N-dialkylcarboxamide, phenyl, and phenyl substituted with one or more groups independently selected from fluoro, chloro, alkyl, fluoroalkyl, alkoxy, fluoroalkoxy, alkylthio, fluoroalkylthio, and N,N-dialkylcarboxamide.

In a more preferred embodiment, each Y is independently selected from the group consisting of a hydrogen atom, fluoro, chloro, $(C_1-C_4)$alkyl, fluoro$(C_1-C_4)$alkyl, $(C_1-C_4)$alkoxy, fluoro$(C_1-C_4)$alkoxy, $(C_1-C_4)$alkylthio, fluoro$(C_1-C_4)$alkylthio, N,N-di$(C_1-C_2)$alkylcarboxamide, phenyl, and phenyl substituted with one or more groups independently selected from fluoro, chloro, $(C_1-C_2)$alkyl, fluoro$(C_1-C_2)$alkyl, $(C_1-C_2)$alkoxy, fluoro$(C_1-C_2)$alkoxy, $(C_1-C_2)$alkylthio and fluoro$(C_1-C_2)$alkylthio.

In an even more preferred embodiment, X bromo and each Y is independently selected from the group consisting of a hydrogen atom, fluoro, chloro, methyl, ethyl, methoxy, ethoxy, trifluoromethyl and trifluoromethoxy.

In a most preferred embodiment, each Y is independently selected from the group consisting of a hydrogen atom, fluoro, chloro, trifluoromethyl and trifluoromethoxy.

Suitable electrophiles are those compounds that react to form a covalent bond with an anionic intermediate such as a compound of formula (III) and that do not contain an acidic proton which can be deprotonated by an anionic intermediate such as compound (III). In a preferred embodiment, the electrophile is selected from the group consisting of an alkyl iodide, a bromoalkyl alkyl ether, an iodoalkyl alkyl ether, an aldehyde, a ketone, a N,N-dialkylamide, an alkyl sulfate, a boron ester, an alkyl disulfide, an aryl disulfide, a nitrile, an alkyl chloroformate, carbon dioxide, a trialkylsilyl chloride, a trialkyitin chloride, sulfur dioxide, sulfonyl chloride and a source of positive halogen. Suitable alkyl iodides include, for example, iodomethane, iodoethane and iodlopropane. Suitable bromoalkyl alkyl ethers include, for example, bromomethyl methyl ether. Suitable iodoalkyl alkyl ethers-include, for example, iodoethyl ethyl ether. Suitable aldehydes include, for example, formaldehyde and benzaldehyde. Suitable ketones include, for example, benzophenone. Suitable N,N-dialkylamides include, for example, N,N-dimethylformamide, N,N-dimethylacetamide and N-formylpiperidine. Suitable alkyl sulfates include, for example, dimethylsulfate. Suitable boron esters include, for example, trimethyl borate and triisopropyl borate. Suitable alkyl disulfides include, for example, methyl disulfide and ethyl disulfide. Suitable aryl disulfides include, for example, phenyl disulfide. Suitable nitriles include, for example, acetonitrile and propiononitrile. Suitable alkyl chloroformates include, for example, methyl chloroformate and ethyl chloroformate. Suitable trialkylsilyl chlorides include, for example, trimethylsilyl chloride. Suitable trialkyltin chlorides include, for example, trimethyltin chloride. Suitable sources of positive halogens include, for example, N-fluorobenzenesulfonimide, N-fluoro-O-benzenedisulfonimide, a N-fluoropyridinium salt, N-chlorosuccinimide, and 2,2,2-trifluoroethyl iodide.

In a preferred embodiment, the residue of the electrophile, Z, is alkyl, more preferably $(C_1-C_6)$alkyl, alkoxyalkyl, more preferably $(C_1-C_3)$alkoxy$(C_1-C_2)$alkyl, alkylthio, more preferably $(C_1-C_3)$alkylthio, phenylthio, formyl, acetyl, benzoyl, carboxyl or carboxylate, chlorosulfonyl, sulfo or sulfonate, alkoxycarbonyl, more preferably $(C_1-C_2)$alkoxycarbonyl, trialkylsilyl, more preferably tri$(C_1-C_4)$alkylsilyl, trialkyltin, more preferably tri$(C_1-C_4)$alkyltin, or halo.

"Alkyl" means a primary alkyl chain and includes, for example, methyl, ethyl, n-propyl, n-butyl, isobutyl, n-amyl and n-hexyl. "Alkoxy" means a linear or branched alkoxy group and includes, for example, methoxy, ethoxy, isopropoxy and n-propoxy. "Alkylthio" means a linear or branched alkyl group attached to a sulfur atom and includes, for example, methylthio, ethylthio, isopropylthio and n-propylthio. "Fluoroalkyl" means a linear or branched alkyl group substituted with one or more fluorine atoms and includes, for example, trifluoromethyl, perfluoroethyl and 2,2,2-trifluoroethyl. "Fluoroalkoxy" means a linear or branched alkoxy group substituted with one or more fluorine atoms and includes, for example, trifluoromethoxy and perfluoroethoxy. "Fluoroalkylthio" means a linear or branched alkyl group, substituted with one or more fluorine atoms, attached to a sulfur atom and includes, for example, trifluoromethylthio and perfluoroethylthio. "N,N-dialkylcarboxamide" means a carboxamide group wherein the nitrogen atom is substituted with two alkyl groups, or two alkyl groups taken together to form a heterocyclic structure containing the nitrogen atom, and includes, for example, diethylcarboxamide, diisopropylcarboxamide and N-formylpiperidine.

Any anhydrous, aprotic solvent may be used in the steps wherein a compound of formula (II) is reacted with sec-butyllithium compound to form a lithiopyridine intermediate of formula (III) and the intermediate of formula (III) is reacted with an electrophile to form a 2-substituted pyridine of formula (I). Suitable aprotic solvents include, for example, ethers such as diethyl ether, tert-butyl methyl ether and ethylene glycol dimethyl ether, cyclic ethers such as tetrahydrofuran and dioxane, and alkanes, such as hexane, heptane and pentane, and aromatic solvents such as cumene, as well as mixtures thereof. Ethers are a preferred solvent.

Usually, an oxygen-free atmosphere is used in the process up until the point wherein the electrophile has completely reacted with the lithio pyridine of formula (III) to form the 2-substitutecl pyridine of formula (I).

The process of both steps (i) and (ii) is conducted at any convenient temperature and is preferably conducted at a temperature of from about −100° C. to about 25° C. More preferred temperatures are those at or less than 0° C. An even more preferred temperature is from about −78° C. to about −30° C. in step (i) and from about −78° C. to about 0° C. in step (ii).

Reaction time for step (i) of the process is from about five minutes to about 12 hours and is somewhat dependent on the size of the reaction and the reactor configuration. Preferably, the reaction time for step (i) is from about one to about six hours and more preferably is from about one hour to about four hours. Reaction time for step (ii) of the process is from about one minute to about two days and is also somewhat dependent on the size of the reaction and the reactor configuration. Preferably, the reaction time for step (ii) is from about one minute to about 12 hours and more preferably is from about one minute to about four hours.

In step (i), the sec-butyllithium is added to a compound of formula (II). In step (ii), the electrophile is added to a compound of formula (III) or the addition can be reversed. However, it is preferred that the electrophile is added to a compound of formula (III).

The following examples are meant to further illustrate the present invention and are not limiting to its scope which is defined by the claims.

EXAMPLE 1

Preparation of 2-Acetyl-5-chloropyridine

A two liter 4 neck flask was equipped with a stirrer, a thermometer and a 250 mL addition funnel. The reaction setup was flushed with nitrogen overnight. A 1.3 M cyclohexane solution of sec-butyllithium (222 mL, 0.289 mol) was charged to the addition funnel with a cannula. 2-Bromo-5-chloropyridine (57.72 g, MW=192.4, 0.30 mol) and 600 mL of ethyl ether were charged to the flask and then cooled in an acetone/dry ice bath. The temperature of the resultant slurry was −76° C. The sec-butyllithium was added dropwise at a rate to maintain the temperature at −74° C. or lower. The addition took 1.5 hours. When the addition was complete the addition funnel was rinsed with 20 mL of ethyl ether, then charged with 30.7 mL of N,N-dimethylacetamide (MW=87.12, d=0.937, 0.330 mol) and 30 mL of ethyl ether. Ten minutes after the completion of the sec-butyllithium addition, the N,N-dimethylacetamide solution was added dropwise to the reaction mixture, again maintaining the temperature at −74° C. or less. This addition took about 40 minutes. The reaction mixture was held at −76° C. for one hour after the N,N-dimethylacetamide addition was complete, then the bath was removed and the temperature allowed to warm to −30° C. At this temperature the cold bath was replaced and the reaction was quenched with 200 mL of 3 N HCl. The reaction mixture was allowed to warm to room temperature and held overnight. The phases were separated, the ethyl ether phase washed with water and saturated brine and then dried over anhydrous MgSO4. The ethyl ether was stripped, the crude product dissolved in methylene chloride and then treated with one weight equivalent of silica gel. The resulting slurry was filtered through Celite and stripped. The product was recrystallized from hexane to give 29.35 g of 2-acetyl-5-chloropyridine (65% yield based on sec-butyllithium, the limiting reagent).

In a comparative run using similar amounts of reagents and procedures, but with the substitution of n-butyllithium for sec-butyllithium, the yield of 2-acetyl-5-chloropyridine amounted to 30%.

EXAMPLE 2

Preparation of 2-Acetyl-5-(trifluoromethyl)pyridine

A 250 mL three neck flask was flushed with nitrogen. A solution of 4.20 g of 2-bromo-5-(trifiluoromethyl)pyridine in 50 ml of anhydrous ethyl ether was cooled to −78° C. The sec-butyllithium (15.8 mL, 1.2M) was added dropwise over 40 minutes and the temperature maintained at −72° C. or lower. When the addition was complete the reaction was held for 10 minutes, then treated with 1.85 mL of N,N-dimethylacetamide in 1.85 ml of ethyl ether while maintaining the temperature at −74° C. or less. The reaction mixture was held at −78° C. for 15 minutes, then the bath was removed and the temperature allowed to warm to 0° C. At this temperature the cold bath was replaced and the reaction was quenched with 20 mL of lN HCl. The reaction mixture was allowed to warm to room temperature and held overnight. The phases were separated, the ethyl ether phase was washed with water and saturated brine, dried over ianhydrous $MgSO_4$ and the ethyl ether stripped. The product was purified by column chromatography to give 0.4 g of 2-acetyl-5-(trifluoromethyl)pyridine as a yellow oil (10% yield). This product contained traces of solvent and roughly 5% of an impurity. Additional, less pure material was also obtained.

Using similar reaction conditions, but substituting n-butyllithium for sec-butyllithium, the reaction of 2-bromo-5-trifluoromethylpyridine on roughly the same scale (4.52 g) gave no desired product.

It should be understood that the instant specification is set forth by way of illustration and not limitation, and that various modifications and changes can be made without departing from the spirit and scope of the present invention as defined by the appended claims.

We claim:
1. A process for preparing a 2-substituted pyridine of formula (I)

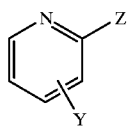

comprising the steps of
(i) reacting a 2-substituted pyridine of formula (II) during a period of from 5 minutes to 12 hours

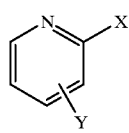

with sec-butyllithium to form a 2-lithiopyridine intermediate of formula (III)

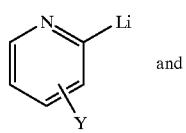

(ii) reacting during a period of from 1 minute to 12 hours a 2-lithiopyridine intermediate of formula (III) with an electrophile, selected from the group consisting of an alkyl iodide, a bromoalkyl alkyl ether, an iodoalkyl tlkyl ether, an aldehyde, a ketone, a N,N-dialkylamide, an alkyl sulfate, a boron ester, an alkyl disulfide, an aryl disulfide, a nitrile, an alkyl chloroformate, carbon dioxide, a trialkylsilyl chloride, a trialkyltin chloride, sulfur dioxide, sulfonyl chloride and a source of positive halogen, to form a 2-substituted pyridine of formula (I) wherein
X is bromo or iodo,
each Y is a group that is not reactive with the lithium compound under the reaction conditions of an anhydrous, aprotic solvent in an oxygen-free atmosphere at a temperature of from $-100°$ C. to $25°$ C., and is indetendently selected from the group consisting of a hydrogen atom, fluoro, chloro, alkyl, fluoroalkyl, trichloromethyl, alkoxy, fluoroalkoxy, alkylthio, fluoroalkylthio, N,N-dialkylcarboxamide, phenyl, and phenyl substituted with one or more groups independently selected from fluoro, chloro, alkyl, fluoroalkyl, alkoxy, fluoroalkoxy, alkylthio, fluoroalkylthio, and N,N-dialkylcarboxamide, and
Z is the residue of the electrophile and is selected from the group consisting of alkyl, alkoxyalkyl, alkylthio, phenylthio, formyl, acetyl, benzoyl, carboxyl or carboxylate, chlorosulfonyl, sulfo or sulfonate, alkoxycarbonyl, trialkylsilyl, trialkyltin, and halo.

2. The process of claim 1 wherein each Y is independently selected from the group consisting of a hydrogen atom, fluoro, chloro, $(C_1-C_4)$alkyl, fluoro$(C_1-C_4)$alkyl, $(C_1-C_4)$alkoxy, fluoro$(C_1-C_4)$alkoxy, $(C_1-C_4)$alkylthio, fluoro$(C_1-C_4)$alkylthio, N,N-di$(C_1-C_2)$alkylcarboxamide, phenyl, and phenyl substituted with one or more groups independently selected from fluoro, chloro, $(C_1-C_2)$alkyl, fluoro$(C_1-C_2)$alkyl, $(C_1-C_2)$alkoxy, fluoro$(C_{1-2})$alkoxy, $(C_1-C_2)$alkylthio and fluoro$(C_1-C_2)$alkylthio.

3. The process of claim 2 wherein each Y is independently selected from the group consisting of a hydrogen atom, fluoro, chloro, methyl, ethyl, methoxy, ethoxy, trifluoromethyl and trifluoromethoxy.

4. The process of claim 3 wherein each Y is independently selected from the group consisting of a hydrogen atom, fluoro, chloro, trifluoromethyl and trifluoromethoxy.

5. The process of claim 1 wherein the electrophile is selected from the group consisting of iodomethane, iodoethane, iodopropane, bromomethyl methyl ether, iodoethyl ethyl ether, formaldehyde, benzaldehyde, benzophenone, N,N-dimethylformamide, N,N-dimethylacetamide, N-formylpiperidine, dimethylsulfate, trimethyl borate, triisopiropyl borate, methyl disulfide, ethyl disulfide, phenyl disulfide, acetonitrile, propiononitrile, methyl chloroformate, ethyl chloroformate, carbon dioxide, trimethylsilyl chloride, trimethyltin chloride, sulfur dioxide and sulfonyl chloride.

6. The process of claim 1 wherein Z is $(C_1-C_6)$alkyl, $(C_1-C_3)$alkoxy$(C_1-C_2)$alkyl, $(C_1-C_3)$alkylthio, phenyithio, formyl, acetyl, benzoyl, carboxyl or carboxylate, chlorosulfonyl, sulfo or sulfonate, $(C_1-C_2)$alkoxycarbonyl or tri$(C_1-C_4)$alkylsilyl.

7. The process of claim 1 wherein X is bromo.

8. The process of claim 1 wherein the anhydrous, aprotic solvent is an ether, a cyclic ether, an alkane, an aromatic solvent or a mixture thereof.

9. The process of claim 8 wherein the solvent is an ether.

* * * * *